United States Patent [19]
Askham

[11] Patent Number: 6,166,267
[45] Date of Patent: Dec. 26, 2000

[54] SYNTHESIS OF N-SILYLATED CYCLOPENTAPHENANTHRENE COMPOUNDS

[75] Inventor: Fredric Askham, Loveland, Colo.

[73] Assignee: Boulder Scientific Company, Mead, Colo.

[21] Appl. No.: 09/389,340

[22] Filed: Sep. 2, 1999

Related U.S. Application Data

[63] Continuation-in-part of application No. 09/018,534, Feb. 4, 1998, Pat. No. 5,965,757.

[51] Int. Cl.$^7$ .............................. C07C 35/42; C07C 35/06
[52] U.S. Cl. ........................... 568/714; 568/838; 585/441
[58] Field of Search .............................. 585/441; 568/714, 568/838

[56] References Cited

PUBLICATIONS

Cope et al., Journal of American Chemical Society, vol. 78, pp. 2547–2551, Jun. 1956.

Primary Examiner—Porfirio Nazario-Gonzales
Attorney, Agent, or Firm—Edward S. Irons

[57] ABSTRACT

A method of converting Compound A (1,3-dehydro-cyclopenta[1]phenanthren-2-one) to Compound C (1H-cyclopenta[1]penanthren) in situ in a single reactor is disclosed.

6 Claims, No Drawings

SYNTHESIS OF N-SILYLATED CYCLOPENTAPHENANTHRENE COMPOUNDS

RELATED APPLICATION

This application is a continuation-in-part of application Ser. No. 09/018,534 filed Feb. 4, 1998 now U.S. Pat. No. 5,965,757.

FIELD OF THE INVENTION

This invention relates to n-silylated cyclopentaphenanthrene Group IV metal complexes. The complexes may comprise metallocene olefin polymerization catalyst ligands.

BACKGROUND OF THE INVENTION

It is known to convert 2,3-dihydro-cyclopenta[1] phenanthren-2-one (CAS Registry No. 37913-11-4; Compound A) to 2,3-dihydro-1H-cyclopenta[1]phenanthren-2-ol (CAS Registry No. 35692-05-8; Compound B) (see Cope, et al., *J.Am.Chem.Soc.* (1956) 78:2547–2551) and to convert Compound B, by treatment with methanesulfonyl chloride, to methanesulfonic acid 2,3-dihydro-1H-cyclopenta[1] phenanthren-2-yl ester (CAS Registry No. 35691-94-2; Compound B-1).

Conversion of Compound B to 1H-cyclopenta[1] phenanthrene (CAS Registry No. 235-92-7; Compound C) is described in Eliassion, et al., *J.Org.Chem.* (1989) 54(1):171–175.

SUMMARY OF THE INVENTION

This invention provides a novel method for the conversion of Compound A to Compound C. The invention may include producing Compound B by reacting Compound A with an alkali metal borohydride in a non-interfering solvent. Compound B may be converted to Compound B1 by reaction in an alkylsulfonyl chloride, chloride, and a trialkylamine.

This reaction produces the intermediate Compound B1. Methane sulfonyl chloride is preferred. Compound B1 is reacted, preferably without isolation from the reaction mixture in which it is produced, with an alkali metal alkoxide to produce Compound C.

Compound C may be further treated to produce n-silylated cyclopentaphenanthrene (1,4-diaryl aliphatic diene) compounds as described in copending application Ser. No. 09/018,534.

GENERAL DESCRIPTION OF THE INVENTION

In general, the invention may comprise a novel three-step method for the production of Compound C.

In a first step, Compound A is converted to Compound B by reaction with an alkali metal borohydride in a non-interfering solvent. Any alkali metal borohydride may be used in the reaction. Sodium borohydride is preferred. The mol ratio of Compound A to alkali metal borohydride is preferably, but not necessarily, about 0.5 to 1.0. The reaction is efficiently conducted at a temperature of −50° C. to 125° C. in any non-interfering solvent of appropriate boiling point under the condition used. Hydrocarbons and ethers are useful. Tetrahydrofuran (THF) is preferred.

In a second step, Compound B is converted to Compound B1 or an analog of Compound B1 by reaction with an alkylsulfonyl chloride and a trialkylamine. Preferably, but not necessarily, the alkylsulfonyl chloride and trialkylamine has from one to five carbon atoms. The trialkylamine is preferably anhydrous.

Methane sulfonyl chloride and anhydrous triethylamine are preferred. In the preferred practice of the invention, about 1 to 3 mols of each of alkylsulfonyl chloride and trialkylamine per mol of Compound B may be used. The step 2 reaction is appropriately conducted at −50° C. to 125° C. The non-interfering solvent is preferably, but not necessarily, the same as that in step 1.

In a third step, Compound B1 or an analog thereof is converted, preferably in situ, in the step 2 reaction mixture in which it is produced to Compound C by treating with an alkali metal alkoxide. Alkali metal alkoxides having 2 to 6 carbon atoms are useful in step 3. Potassium tertiary butyl alkoxide is preferred. One to three mols of alkali metal alkoxide per mol of Compound B1 may used. Compound C may be isolated in known manner from the step 3 reaction mixture.

EXEMPLIFICATION OF THE INVENTION

EXAMPLE 1

Conversion of Compound A to Compound B

1. Charge 393 grams (10.34 moles) of sodium borohydride to vessel.

2. Charge 15.0 kgs (16.9 liters) of THF to the same vessel as in (1) to form a slurry.

3. Stir the step 2 slurry of THF and sodium borohydride for 2 hours.

4. In a separate vessel, charge 4.0 kgs (17.24) moles of Compound A.

5. Charge to the vessel containing the Compound A from step 4, 55 kgs (61.8 liters) of THF.

6. Cool the vessel containing the sodium borohydride/THF mixture to 15 to 25° C.

7. Feed the sodium borohydride slurry of step 3 to Compound A contained in the vessel of steps 4 and 5.

8. Rinse the vessel which contains the borohydride with 15 kgs of THF, and send the rinse to the step 4 vessel containing the Compound A.

9. Stir for 3 hours.

10. Charge 30 kgs of water to a clean vessel.

11. Charge 9.0 kgs of sodium chloride to the vessel in (10).

12. To the vessel in (10), add 6.45 kg (3.6 liters) of concentrated hydrochloric acid. Maintain the vessel to below 30° C. during addition.

13. Feed the HCl/water/NaCl solution to the step 7 vessel containing the Compound A/borohydride/THF mixture over a period of 15 minutes, keeping the pot temperature <30 degrees with full tower cooling, vessel vent open with a nitrogen sweep.

14. Stir the solution from (13) for 30 minutes, and settle for 20 minutes.

15. Separate off the lower aqueous layer from (14).

16. Make up a solution 5 kgs water and 1.6 kgs of 50% sodium hydroxide; to this solution, add 1.5 kgs of sodium chloride.

17. Feed the solution from (16) to the Compound A/borohydride/THF solution in step (13).

18. Separate off the lower aqueous layer from (17).

19. To the solution in (17), add 2.0 kgs of sodium sulfate.

20. Stir the solution in (19) for 1 hour.

21. Filter the solution in (20).

22. Distill 45 kgs of THF atmospherically from the solution in (21) to provide a residual THF solution of Compound A.

23. To another vessel, charge 50 kg (69.4 liters) in Isopar, and heat the pot to a temperature of 100–105° C.

24. To flush off the residual THF, slowly feed the Compound A solution in (22) at 55–60° C. to the vessel containing Isopar (23) to afford the alcohol (Compound B) as a filterable powder.

25. Bring the final pot temperature in (24) to 115° C. after all of the Compound A solution (22) has been fed in. Hold for 30 minutes at 120° C. Cool to 15–20° C.

26. Filter the solution from (25) through a buchner, and wash the filter cake 2 times with hexane.

27. Isolate the Compound B in the buchner.

Yield of experiment: 95–97% of theory.

EXAMPLE 2

Conversion of Compound B to Compound C

1. Charge 76.9 moles of Compound B to a clean, dry, nitrogen purged vessel (vessel A).

2. Charge 255 kgs of tetrahydrofuran to the vessel.

3. Charge 11.7 kgs (115.6 moles) of triethylamine to the vessel.

4. Charge 11.1 kgs (96.9 moles) of methanesulfonyl chloride to the vessel.

5. Heat the vessel to reflux and stir for one hour.

6. To a second vessel (vessel B), charge 30.3 kgs (270.1 moles) of potassium t-butoxide and 90 kgs (101.2 liters) of THF. Agitate until all of the potassium t-butoxide dissolves.

7. Feed the mesylate solution contained in vessel A to vessel B keeping the temperature below 40° C.

8. Stir the solution in vessel B for 2 hours at 30–35° C.

9. Add to vessel B, 180 kgs of water. 10. Charge to vessel B, 62.5 kgs of sodium chloride while maintaining the pot temperature below 30° C.

11. Agitate vessel B for 20 minutes.

12. Settle the contents of vessel B for 40 minutes.

13. Separate the lower aqueous layer in vessel B, keeping any rag layer with the aqueous.

14. To vessel B, charge 5 kgs of sodium sulfate, and stir the contents for 30 minutes.

15. Filter the contents of vessel B into a nitrogen purged drum.

Yield of experiment: 95–97% of theory.

I claim:

1. A method which comprises reacting 1,3-dehydrocyclopenta[1]phenanthren-2-one with an alkali metal borohydride in a tetrahydrofuran, wherein a reaction mixture containing 2,3-dihydro-1H-cyclopenta[1]phenanthren-2-ol is produced.

2. The method of claim 1, wherein the alkali metal borohydride is sodium borohydride.

3. The method of claim 1 or claim 2, wherein the mole ratio of said alkali metal borohydride to said 1,3-dehydrocyclopenta[1]phenanthren-2-one is from about 0.5 to 1.0.

4. The method which comprises:

(i) treating 2,3-dihydro-1H-cyclopenta[1]phenanthren-2-ol with sulfonyl chloride and an anhydrous trialkylamine in a non-interfering solvent, wherein a first reaction mixture containing methanesulfonic acid 2,3-dihydro-1H-cyclopenta[1]phenanthren-2-yl ester is produced; and (ii) treating said step (i) reaction mixture with potassium t-butoxide in a non-interfering solvent, wherein a second reaction mixture containing 1H-cyclopenta[1]phenanthren is produced.

5. The method of claim 4 in which steps (i) and (ii) are conducted sequentially in the same reactor and without separation of said methanesulfonic acid 2,3-dihydro-1H-cyclopenta[1]phenanthren-2-yl ester from said first reaction mixture.

6. The method of claim 4 or claim 5 in which the non-interfering solvent is tetrahydrofuran.

* * * * *